United States Patent [19]
Levine

[11] Patent Number: 5,350,401
[45] Date of Patent: Sep. 27, 1994

[54] IMPLANTABLE CARDIOVERTER/DEFIBRILLATOR DEVICE HAVING MEANS FOR DETERMINING AND TREATING LOW AMPLITUDE VENTRICULAR FIBRILLATION AND METHOD THEREOF

[75] Inventor: Paul A. Levine, Santa Clarita, Calif.

[73] Assignee: Siemens Pacesetter, Inc., Sylmar, Calif.

[21] Appl. No.: 37,211

[22] Filed: Mar. 26, 1993

[51] Int. Cl.$^5$ .............................................. A61N 1/39
[52] U.S. Cl. ........................................... 607/4; 607/14
[58] Field of Search ............................ 607/4, 9, 14, 27; 128/697

[56] References Cited

U.S. PATENT DOCUMENTS

| | | | |
|---|---|---|---|
| 4,686,988 | 8/1987 | Sholder | 128/419 |
| 4,712,555 | 12/1987 | Thornander et al. | 128/419 |
| 4,712,556 | 12/1987 | Baker | 128/419 |
| 4,787,389 | 11/1988 | Tarjan | 128/419 |
| 4,788,980 | 12/1988 | Mann et al. | 128/419 |
| 4,899,750 | 2/1990 | Ekwall | 128/419 |
| 4,940,052 | 7/1990 | Mann et al. | 128/419 |
| 4,944,298 | 7/1990 | Sholder | 128/419 |
| 4,989,602 | 2/1991 | Sholder et al. | 128/419 |

*Primary Examiner*—William E. Kamm
*Attorney, Agent, or Firm*—Lisa P. Weinberg

[57] ABSTRACT

An ICD/pacemaker device provides a shocking pulse whenever it senses cardiac activity indicative ventricular fibrillation by standard means and a unique algorithm to respond to low amplitude ventricular fibrillation that would not be expected to be recognized/sensed by standard means. The ICD/pacemaker device further provides stimulation pulses on demand to a patient's heart whenever cardiac activity is not sensed and determines whether a given stimulation pulse has caused capture. If capture has not occurred, the energy of the stimulation pulse is increased by a predetermined amount and capture is retested. If the energy of the stimulation pulses increases up to a maximum value without causing capture, the generation of further stimulation pulses is stopped, and the ICD/pacemaker device presumes that low amplitude ventricular fibrillation is present. When fibrillation is sensed or presumed to be present, a shocking pulse is generated. In this manner, the ICD/pacemaker device responds to a low amplitude ventricular fibrillation that may not be sensed by the normal sensing circuits.

20 Claims, 5 Drawing Sheets

IMPLANTABLE CARDIOVERTER/DEFIBRILLATOR DEVICE HAVING MEANS FOR DETERMINING AND TREATING LOW AMPLITUDE VENTRICULAR FIBRILLATION AND METHOD THEREOF

FIELD OF THE INVENTION

The present invention relates to implantable stimulation devices and methods and, more particularly, to an implantable cardioverter defibrillator (ICD) device that is capable of detecting and treating low amplitude fibrillation.

BACKGROUND OF THE INVENTION

Bradycardia is a condition of the heart where the heart beat slows to a rate that is considered insufficient to pump an adequate supply of blood through a patient's body. A heart rate of less than 50 beats per minute is considered as a bradycardia condition for most patients.

One common technique for treating bradycardia is to implant a pacemaker in the patient. The pacemaker senses cardiac electrical activity, which electrical activity normally accompanies a heart beat. If the cardiac electrical activity is not sensed, it indicates that the heart is not beating at a prescribed rate. Stimulation pulses are then generated and delivered to an appropriate heart chamber, either the atrium or the ventricle, in order to stimulate the muscle tissue of the heart to contract, thereby forcing the heart to beat at a rate that is faster than the intrinsic rate. A pacemaker operating to maintain the heart rate at a rate that is faster than a bradycardia rate is referred to as a bradycardia-support pacemaker.

Bradycardia-support pacing is realized in a pacemaker by defining a period of time, referred to generally as the "escape interval," that is slightly longer than the period of time between heart beats of a heart experiencing bradycardia. For example, if the heart is beating at a rate of 50 beats per minute, the time period between consecutive heart beats is 1200 milliseconds. Thus, in a bradycardia-support pacemaker, if it is desired that the heart rate never slow to a rate less than 50 beats per minute, the escape interval of the pacemaker is set to an appropriate value that causes a stimulation pulse to always be generated if more than 1200 milliseconds elapse since the last sensed heart beat. If a heart beat occurs before 1200 milliseconds have elapsed, then that indicates the heart is beating at a rate faster than 50 beats per minute, and no stimulation pulse need be generated. Upon electrically sensing such a "natural" (non-stimulated) heart beat within the allotted time period, the escape interval is reset, and a new escape interval is started. A stimulation pulse will be generated at the conclusion of this new escape interval unless a natural heart beat is again sensed during the escape interval. In this way, stimulation pulses are generated "on demand," i.e., only when needed, in order to maintain the heart rate at a rate that never drops below the rate set by the escape interval.

The heart rate is monitored by examining the electrical signals corresponding to the depolarization of the cardiac muscle tissue. The depolarization of the cardiac muscle tissue triggers the mechanical contraction of the cardiac muscle tissue. The electrical signal corresponding to the depolarization of the atrial muscle tissue is identified as a P-wave on a surface EKG. The electrical signal corresponding to the depolarization of the ventricular muscle tissue is identified as an R-wave on a surface EKG. The sequence of electrical signals, corresponding to P-waves followed by R-waves, can be sensed from inside of or directly on the heart by using sensing leads having appropriate electrodes that are implanted inside or on the heart, e.g., pacemaker leads. The electrical signals corresponding to P-waves and R-waves sensed internal to or directly on the heart are referred to as the electrogram (EGM) of the heart.

A pacemaker includes means for sensing P-waves and/or R-waves, and hence means for monitoring the patient's EGM. From such EGM, the physical activity of the heart (i.e., a muscle contraction of a given heart chamber, atrium and/or ventricle) can be deduced. In order to determine the heart rate, for example, the pacemaker measures the time that elapses between consecutive R-waves. The R-wave is normally used for this determination because the R-wave is normally a much larger electrical signal than the P-wave, and is hence much easier to sense. However, the same rate determination can also be made by measuring the time between consecutive P-waves, if desired.

R-waves and/or P-waves are sensed by placing an electrode in contact with, or in proximity to, the cardiac tissue of interest. Most pacemakers use the same electrode for sensing R-waves and/or P-waves, as is used to deliver stimulation pulses to the ventricle and/or atrium, respectively, although separate sensing and stimulation electrodes could and have been used. In order to prevent electrical noise or other low level electrical signals from being sensed as electrical cardiac activity when in fact cardiac electrical activity (e.g., an R-wave) has not occurred, it is necessary to define a threshold level above which the amplitude (and/or other characteristics) of a sensed electrical signal must go before such signal is recognized as an indicator of cardiac electrical activity. Unfortunately, the use of threshold detection in this manner sometimes precludes the detection of a valid low-level R-wave, or other valid cardiac electrical signal, that is below the set threshold level. While every attempt is made to set the threshold level so as to minimize missing the detection of valid cardiac electrical signals, the threshold level cannot be set so low so as to commonly detect noise or other invalid signals as valid signals. Hence, a tradeoff must be made, and usually such tradeoff favors not sensing noise or other invalid signals, thus potentially missing valid low level cardiac electrical signals. Hence, as a practical matter, most pacemakers are set such that they will occasionally fail to sense a valid low level R-wave and/or P-wave.

It is noted that all modern implantable pacemakers are programmable. That is, the basic escape interval of the pacemaker, as well as the threshold level of the sensing circuits used in the pacemaker, as well as numerous other operating parameters of the pacemaker, may be programmably set at the time of implantation or thereafter to best suit the needs of a particular patient.

Recently, there has also been much interest shown in implantable cardioverter defibrillation (ICD) systems. An ICD system provides one or more high energy shocking pulses to a heart when: (1) the ICD senses that the heart is beating fast (tachycardia); or (2) the ICD senses that the heart is beating in a rapid, chaotic manner (fibrillation). (Note, that an ICD device senses electrical cardiac activity, just as does a pacemaker, and determines the heart rate by measuring the time interval between consecutive R-waves. When the ICD senses ventricular fibrillation—a very rapid, chaotic R-wave rate—the mechanical effect on the heart is cardiac arrest, i.e., the heart muscles do not contract effectively, and blood is not pumped through the body.)

It is noted that the high energy shocking pulse delivered by an ICD device has an energy content on the order of joules, whereas the stimulation pulse delivered by a pacemaker has an energy content on the order of microjoules. In order to clearly distinguish the low energy pacing pulses of a pacemaker from the high energy shocking pulses delivered by an ICD device, the pacemaker pulses will be referred to herein as "stimulation pulses" and the ICD pulses will be referred to as "shocking pulses."

The purpose of delivering a high energy shocking pulse during ventricular tachycardia, ventricular fibrillation, or other tachyarrhythmias is to break or stop the tachycardia, fibrillation, or other tachyarrhythmia. Tachycardia, fibrillation, and other tachyarrhythmias are sustained by an imbalance in the recovery and conduction among the various tissue of a given heart chamber, typically the ventricle. Such imbalance is referred to as temporal dispersion of refractoriness. The high energy shocking pulse depolarizes any tissue which is not depolarized at that moment. That is, it puts all of the tissue (or a large percentage of the tissue) into the same physiologic state (depolarized) and thus, when such tissue recover or repolarize, it will be able to be activated or depolarized in a synchronized or coordinated manner.

In the case of a tachycardia, the delivery of the shocking pulse or pulses by the ICD is usually referred to as "cardioversion," and the shocking pulse is typically delivered in synchrony with the heart's R-wave in order to avoid delivering the shocking pulse to the heart during the T-wave portion of the cardiac cycle. (The T-wave portion is that portion of the cardiac cycle, following the R-wave during which the massive ventricular tissue is repolarizing.) The reason that one tries to avoid delivering a high energy shocking pulse (or even a low energy shocking pulse or a pacemaker stimulation pulse) onto the T-wave is that such action could have a paradoxical effect and further accelerate the heart rhythm. That is, a slow ventricular tachycardia might be accelerated to a faster ventricular tachycardia, and/or a faster ventricular tachycardia might be accelerated to ventricular fibrillation.

In the case of fibrillation, there is a chaotic and rapid beating of the many individual muscle fibers of the heart, and the heart is consequently unable to maintain effective synchronous contraction, and is thus not able to pump blood. For all practical purposes, the heart has mechanically stopped, although (as indicated above) electrically it is very active with multiple chaotic electrical signals. Hence, the purpose of delivering a shocking pulse or pulses to the heart during fibrillation (also commonly referred to as "defibrillation" pulses) is synchronize or coordinate the cardiac tissue so that the many individual muscle fibers can once again maintain effective synchronous contractions, and thereby efficiently pump blood through the patient's body.

Conventional ICD devices known in the art typically include a built-in sensor circuit. Such sensor circuit is designed to sense, through attached sensing electrodes, the rate at which the heart is beating. If the sensed heart rate exceeds a high fixed rate threshold (i.e., if a tachycardia is sensed), the ICD is designed to deliver a low energy shocking pulse, commonly referred to as a cardioversion pulse. If fibrillation is detected, the ICD is designed to deliver a high energy shocking pulse, or shocking pulse. Typically, a cardioversion pulse will be a lower energy discharge than will a shocking pulse.

For a patient having both a bradycardia support pacemaker and an ICD device, a potential problem occurs when there is a low amplitude fibrillation that is not recognized by the sensing circuits of the pacemaker (i.e., a very fast chaotic heart rhythm that is of such a low amplitude that the sensing circuits of the pacemaker cannot sense it). As far as the pacemaker is concerned, no cardiac activity is occurring because none is sensed. If the ICD is able to "see" these signals, it will respond appropriately. If, however, the ICD also fails to "see" the low amplitude fibrillation signals (and does not respond), then the pacemaker circuits will interpret this lack of activity as asystole and release an output stimulation pulse. If the patient is really fibrillating, such output stimulation pulse will be ineffective. However, if the ICD device now "sees" (i.e., senses) the output stimulation pulse, its circuits will interpret such ineffective stimulation pulse as an R-wave, and will thus not charge up nor release a shocking pulse. Furthermore, if the ICD does not "see" the low amplitude ventricular fibrillation, it will remain quiescent. Hence, the fibrillation goes undetected and untreated.

For a patient having a combination implantable stimulation device that includes both the bradycardia, cardioversion and defibrillation functions, a similar problem exists in that the electrogram signal from the ventricular fibrillation may be so low in amplitude that neither the ICD nor the pacemaker sensing circuits sense anything, thus causing the pacemaker portion of the system to release a stimulation pulse. Upon releasing the stimulus, the automatic gain feature of the ICD/pacemaker sensing circuits, if enabled, incrementally increases its sensitivity to its most sensitive setting, in an attempt to "look" for an R-wave. If a failure to sense an R-wave persists, the diagnosis is "true asystole," and the ICD/pacemaker will continue to release stimulation pulses at its programmed rate. Unfortunately, if the rhythm is truly ventricular fibrillation with a EGM signal that is too low to be sensed by either the pacemaker portion of the device or the ICD component, the stimulation pulses of the pacemaker will not be effective. However, the pacemaker does not know that its pacing stimulation pulses are ineffective, so it will just continue to deliver such ineffective pacing stimuli.

What is needed, therefore, is a pacemaker/ICD device or system wherein a proper response to an alleged asystole can occur, and wherein the pacemaker/ICD device can ascertain whether or not a given stimulation pulse is effective, i.e., whether it "captures" the heart.

SUMMARY OF THE INVENTION

The present invention provides an ICD/pacemaker device that includes the functions of both an implantable cardioversion/defibrillation (ICD) device and an implantable pacemaker. Such pacemaker/ICD device advantageously provides a response to a low amplitude fibrillation condition calculated to effectively detect and treat such fibrillation condition.

Advantageously, like conventional ICD devices, the ICD/pacemaker device of the present invention provides a shocking pulse (a shocking pulse) whenever cardiac activity is sensed that is indicative of ventricular fibrillation. Further, like conventional pacemaker devices, the ICD/pacemaker device of the invention also provides stimulation pulses on demand to a patient's heart whenever cardiac activity is not sensed within a prescribed escape interval. Unlike conventional ICD and pacemaker devices, however, the ICD/pacemaker device of the present invention includes means for determining whether a given stimulation pulse generated by the device has caused capture. If not, the energy of the stimulation pulse is increased until capture is realized. Should the energy of the stimulation pulses be increased up to a maximum value without effectuating capture, further generation of the stimulation pulses is stopped, and the ICD/pacemaker device assumes that ventricular fibrillation is present.

More specifically, if a low amplitude ventricular fibrillation condition develops (i.e., one that is of insufficient amplitude to be sensed by the pacemaker/ICD sensing circuits), then pacemaker side of the device "sees" asystole and in response issues a stimulation pulse. At the same time, an automatic gain feature of the device increases the sensitivity of the system so that lower and lower amplitude EGM signals may be detected. If still nothing is sensed, the pacemaker continues to see asystole, causing another stimulation pulse to be released. In the present invention, an autocapture feature determines whether capture has occurred with each pacing stimulus. In the presence of true ventricular fibrillation, a pacing stimulus will be ineffective and so the autocapture feature detects "noncapture," causing the pulse generator to increase the magnitude of the stimulation pulses that it generates. In one embodiment, the ICD/pacemaker will generate a predetermined number of stimulation pulses, each with increasing energy, to determined the cause of the "loss of capture." If capture occurs, then a new threshold level is determined by progressively lowering the energy level until capture is lost, to which an appropriate safety margin is then added. If, however, there is still no evidence of capture (which would likely be the case for true ventricular fibrillation), the pacemaker/ICD logic circuits then conclude that low amplitude ventricular fibrillation must be present. In response to such conclusion, a shocking pulse is released. Such shocking pulse should be effective if the heart is undergoing low amplitude ventricular fibrillation.

In the preferred embodiment, the predetermined number of stimulation pulses having increasing energy levels is at least one pulse of maximum energy, or at least one pulse with an energy level that is expected to guarantee capture and at which an evoked response can still be detected. Since only one pulse is delivered, the system can rapidly determine the cause of "loss of capture." The system may also verify capture over a series of pulses at the desired energy level to ensure that a single failure will not prematurely disable the system. If capture does not occur over the desired number of pulses, then the pacemaker/ICD logic circuits then conclude that low amplitude fibrillation must be present.

According to one aspect of the present invention, the ICD/pacemaker generates a shocking pulse to shock the heart back into a normal rhythm whenever ventricular fibrillation is sensed to be present, or whenever ventricular fibrillation is assumed to be present. In this manner, appropriate therapy—either in the form of stimulation pulses on demand or shocking pulses as required—is advantageously afforded to the patient.

According to another aspect of the invention, the ICD/pacemaker device concludes that ventricular fibrillation is present whenever capture is not achieved after applying at least one higher energy stimulation pulse to the heart. Advantageously, by making such conclusion, the ICD/pacemaker device detects and responds to a low amplitude ventricular fibrillation that may not otherwise be detectable by the normal sensing circuits of the device.

It is noted that as used herein, the term "capture" refers to the ability of a given stimulation pulse generated by the ICD/pacemaker device to depolarize the myocardium, i.e., to cause the heart to "beat." While there are many factors that influence whether a given stimulation pulse effectuates capture, one of the principle factors is the energy of the stimulation pulse. The energy of the stimulation pulse, in turn, is determined by the amplitude and width of the stimulation pulse generated by the ICD/pacemaker. Advantageously, in a programmable pacemaker, both the amplitude and pulse width of the stimulation pulse are parameters that may be programmably controlled or set to a desired value. To conserve the limited energy stored within the battery of the ICD/pacemaker device, it is generally preferred that the energy of the stimulation pulse be adjusted as low as possible while still maintaining an adequate margin of safety.

One embodiment of the present invention may thus be characterized as a method for determining a particular type of cardiac fibrillation characterized by low amplitude cardiac activity that cannot be readily sensed by conventional sensing means. Such method is designed for use within an implantable pacing device. The implantable pacing device includes sensing means for sensing cardiac activity, and pacing means for generating pacing pulses on demand. The method includes the steps of: (a) generating a pacing pulse if the sensing means fails to sense cardiac activity during a preset escape interval; (b) determining if the pacing pulse generated in step (a) has effectuated capture; and (c) concluding the presence of the particular type of cardiac fibrillation in the event the pacing pulse generated in step (a) has not effectuated capture.

Another embodiment of the invention may be characterized as a method for use within an implantable cardioversion device (ICD) for detecting and responding to ventricular fibrillation in the presence of a bradycardia-support pacing system when the R-waves associated with such ventricular fibrillation are sufficiently low in amplitude to prevent their being sensed by the bradycardia-support pacing system, which bradycardia-support pacing system delivers pacing pulses in the absence of sensed R-waves. Such method includes the steps of:

(a) determining if a given pacing pulse generated by the bradycardia-support pacing system has effectuated capture;

(b) delivering a pacing pulse having an increased energy level in the event capture is not realized in step (a) and repeating step (a) with the increased energy level pacing pulse; and (c) in the event capture is not realized, delivering a shocking pulse from the ICD.

Still a further embodiment of the invention may be characterized as an implantable pacing and cardioversion device. Such pacing and cardioversion device includes: (a) sensing means for sensing cardiac activity; (b) pacing means for generating pacing pulses on demand; (c) defibrillation means for generating shocking pulses upon sensing cardiac activity indicative of a first type of cardiac fibrillation characterized by a sustained rhythm of sensed cardiac activity at a rate faster than a prescribed rate; and (d) determining means for determining the presence of a second type of cardiac fibrillation characterized by a low amplitude cardiac activity that cannot be sensed by the sensing means. The determining means of such embodiment includes: (i) capture-determining means for determining if a given pacing pulse generated by the pacing means has effectuated capture; and (ii) decision-determining means responsive to the capture-determining means for determining the presence of the second type of cardiac fibrillation.

It is thus a feature of the present invention to provide an implantable pacing and cardioversion device and/or method that automatically affords a patient appropriate therapy, either in the form of stimulation pulses on demand or shocking pulses as required.

It is another feature of the invention to provide an implantable pacing and cardioversion device and/or method that not only provides stimulation pulses on demand, but that also ascertains the presence of, and responds to, ventricular fibrillation, regardless of whether such ventricular fibrillation is characterized by high or low amplitude R-waves.

It is still another feature of the invention to provide an implantable device and/or method that presumes the presence of low amplitude ventricular fibrillation when the amplitude of the R-waves associated with such ventricular fibrillation is too low to be sensed and when capture is not achieved using a stimulation pulse having an increased energy level.

It is yet another feature of the invention to provide an implantable pacemaker and cardioversion device that includes means for determining whether a given pacing pulse has effectuated capture.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims. In the description of the invention that follows, like numerals or reference designators will be used to refer to like parts or elements throughout.

Figure 1:
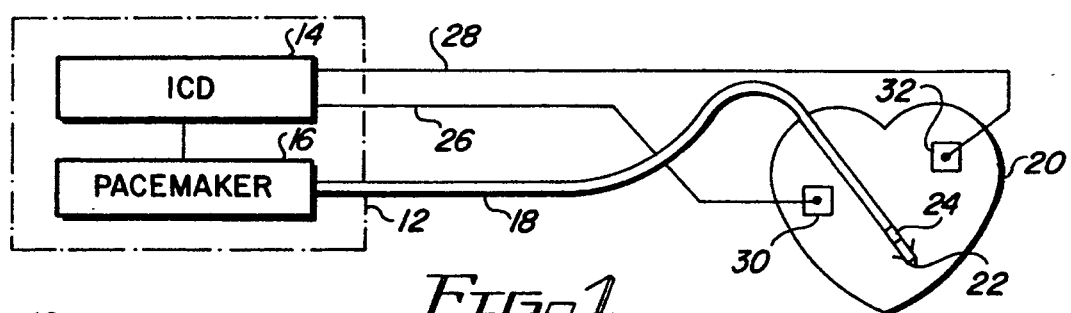
FIG. 1 shows an ICD/pacemaker device connected to a heart.

According to one embodiment of the present invention, there is provided an implantable cardioversion device (ICD) that is combined with an implantable pacemaker. Such a combined device, referred to as an "ICD/pacemaker device" is illustrated in FIG. 1. As seen in FIG. 1, an ICD/pacemaker device 12 includes an ICD circuitry 14 and a pacemaker circuitry 16. The pacemaker circuitry 16 is connected to a pacing lead 18 that couples the pacemaker circuitry 16 to a heart 20. The lead 18 is typically implanted transvenously so as to reside inside of a prescribed chamber of the heart, e.g., the right ventricle. A lead implanted inside the heart is referred to as an endocardial lead. However, for purposes of the present invention, the pacing lead 18 may also be placed external to the heart, in which case it is referred to as an epicardial lead.

The lead 18, shown in FIG. 1, includes a distal electrode 22 and a ring electrode 24, both of which electrodes are positioned so as to be in contact with cardiac tissue and/or fluids. It is to be understood that while only a single pacemaker lead 18 is shown in FIG. 1, positioned so as to reside in the ventricle, such illustration is only exemplary. As is known in the pacing arts, a plurality of pacing leads may be used, as required, to sense and pace in one or more desired heart chambers. Further, as is known in the art, such pacing may be performed either unipolarly, bipolarly, or combinations thereof. The present invention may advantageously be used with all such pacing configurations.

The ICD circuitry 14 is typically coupled to the heart 20 through a pair of "defibrillation" leads 26 and 28. Generally, such leads have previously been realized using epicardial leads, as suggested in FIG. 1. However, for purposes of the present invention either epicardial or endocardial defibrillation leads 28 and 26 could be used. A suitable electrode 30 connects the lead 26 to the heart 20. Similarly, a suitable electrode 32 connects the lead 28 to the heart 20. The electrodes 30 and 32 shown in FIG. 1 are depicted as "patch" electrodes, but any type of electrode suitable for use with an ICD device to defibrillate the heart could be used.

Figure 2:
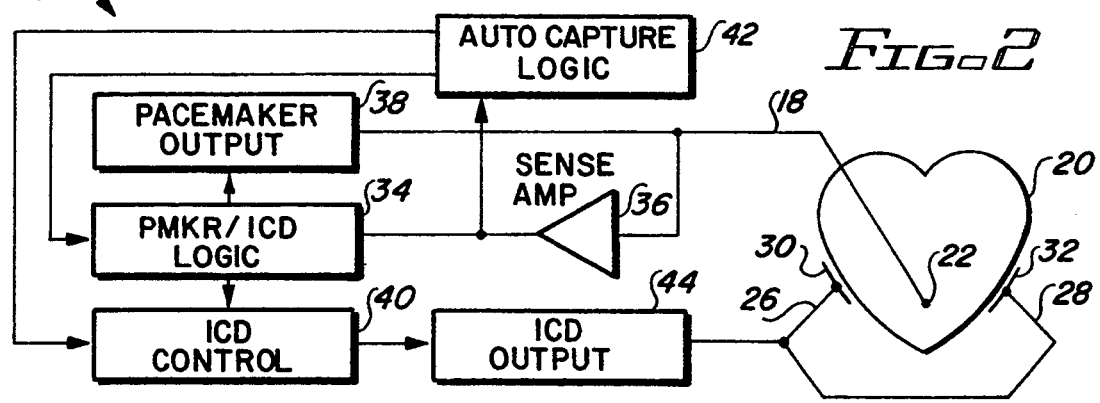
FIG. 2 is a simplified functional block diagram of an ICD/pacemaker device made in accordance with the present invention.

Referring next to FIG. 2, a simplified functional block diagram of the ICD/pacemaker device 12 is shown. The diagram is simplified in the sense that only those functions that relate to the present invention are illustrated. Other well-known functions, common to all pacing or cardioversion devices, are not shown.

The control of the ICD/pacemaker device 12 is performed by a logic control circuit 34, labeled "Pmkr/ICD Logic," and hereafter referred to as the "control logic" 34. The control logic 34 monitors the heart 20 through a sense amplifier 36. That is, whenever cardiac activity occurs, such as an R-wave, such activity is sensed through the electrode 32 of the pacing lead 18 and the sense amplifier 36.

The control logic 34 controls the timing at which the heart 20 is stimulated by generating a first trigger signal and delivering such first signal to a pacemaker output circuit 38. The pacemaker output circuit 38, in response to the trigger signal, generates a stimulation pulse of a prescribed pulse width and amplitude, and delivers such stimulation pulse to the heart 20 over the pacing lead 18.

The control logic 34 also controls when a shocking pulse is delivered to the heart 20 by generating a second trigger signal whenever a ventricular fibrillation (or ventricular tachycardia which necessitates a shocking pulse to terminate it) is sensed. Such second trigger signal is presented to an ICD control circuit 40. The ICD control circuit 40, in combination with the auto capture logic 42, performs the function of determining whether a shocking pulse should be generated and delivered to the heart 20. If so, a shocking trigger signal is generated and presented to an ICD output circuit 44, whereupon a shocking pulse is generated and delivered to the heart over the defibrillation leads 26 and 28.

According to the present invention, the ICD control circuit 40 responds to two types of ventricular fibrillation. The first type is characterized by the sensing of R-waves at a very rapid rate, and may be considered as a "sensed" ventricular fibrillation. The R-waves are sensed through the amplifier 36. The rate at which the R-waves occur is determined by the control logic 34. If the rate of the sensed R-waves exceeds a prescribed threshold, then the second trigger signal is generated. In response to the second trigger signal, the ICD control circuit generates the shocking trigger signal that enables the ICD output circuit to generate a shocking pulse at the appropriate time.

The second type of ventricular fibrillation to which the ICD control circuit 40 responds is low amplitude ventricular fibrillation. Low amplitude ventricular fibrillation is characterized by very low amplitude R-waves that are not sensed by the sense amplifier 36, and may be considered as a presumed ventricular fibrillation. The presence of this second type of ventricular fibrillation is presumed because it cannot be sensed by conventional sensing means, that is, R-waves associated with such second type of ventricular fibrillation are so low in amplitude that they cannot be sensed by the sense amplifier 36. However, even through the R-waves cannot be sensed, the presence of other factors in combination with the failure to sense R-waves leads to the reasonable presumption that such second type of ventricular fibrillation is present.

A key element of the present invention that facilitates the recognition of the second type of ventricular fibrillation (the "presumed" ventricular fibrillation) is the auto capture logic 42. The auto capture logic 42 determines whether a given stimulation pulse, generated by the pacemaker output circuit 38, has caused capture. Two output signals are provided by the auto capture logic 42, one directed to the control logic 34, and the other directed to the ICD control circuit 40. Both output signals provide an indication whether capture has occurred or not. If capture occurs, then operation of the ICD/pacemaker device 12 continues in its normal pacing mode, that is, stimulation pulses are generated on demand as needed by the heart 20, and shocking pulses are not generated. If capture does not occur, the control logic 34 responds by increasing the amplitude and/or pulse width of the next stimulation pulse that is delivered to the heart 20, thereby increasing the energy of the applied stimulation pulse. If capture still does not occur after the energy of the stimulation pulse has been raised to a prescribed level, for example, the maximum possible level at which capture detection can occur, then the presence of the second type of ventricular fibrillation is presumed.

In response to determining that the second type of ventricular fibrillation is present, the control logic 34 stops generating the first trigger signal (in order to cease further generation of the stimulation pulses) and the ICD control circuit 40 is enabled to generate its shocking trigger signal. Such shocking trigger signal causes the ICD output circuit to generate and deliver a shocking pulse to the heart. If the first shocking pulse is ineffective, then the ICD control circuit 40 continues to trigger the generation of shocking pulses at an appropriate rate until cardiac activity is sensed through the sense amplifier 36 or until a predetermined number of shocks have been delivered to the heart.

Figure 3:
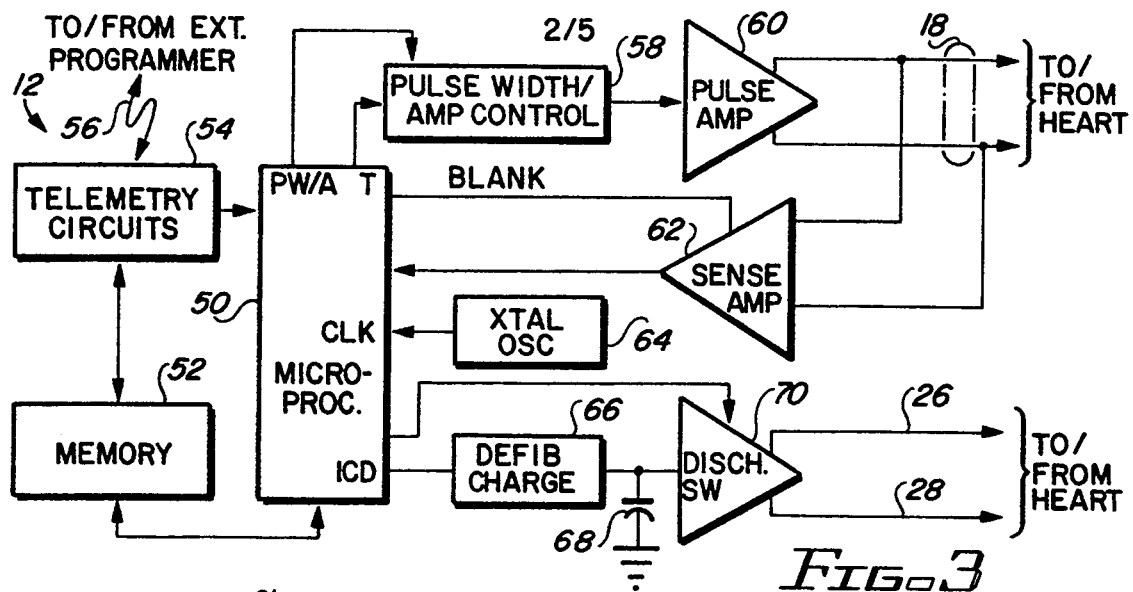
FIG. 3 is a block diagram of one embodiment of the present invention that performs the functions of the ICD/pacemaker device of FIG. 2.

In FIG. 3, a simplified block diagram of one embodiment of the ICD/pacemaker device 12 according to the present invention is shown. FIG. 3 is "simplified" in the sense that only those elements or components that directly relate to the present invention are shown. A more detailed description of a pacemaker and its operation may be found, for example, in U.S. Pat. Nos. 4,712,555; 4,788,980; 4,940,052; 4,944,298, which patents are incorporated herein by reference. A more detailed description of an ICD may be found, for example, in U.S. Pat. Nos. 4,787,389 or 4,989,602. The '602 patent is entitled "Programmable Automatic Implantable Cardioverter/Defibrillator and Pacemaker System" and is assigned to the same assignee as the present application. The '602 patent is incorporated herein by reference.

The embodiment of the ICD/pacemaker device 12 shown in FIG. 3 is a microprocessor-based embodiment. As such, it includes a microprocessor circuit 50 coupled to a suitable memory device 52. The microprocessor 50 is programmed to provide the functions of the control logic 34, the ICD control circuit 40, and the auto capture logic 42 described above in connection with FIG. 2. Advantageously, suitable telemetry circuits 54 allow the microprocessor 50 and the memory device 52 to be programmed with appropriate operating parameters and control data so that a desired performance is achieved. Such programming occurs through the use of a suitable external programmer, not shown, which establishes a communication link, represented by the wavy arrow 56, between the telemetry circuits 54 and the external programmer. When such link 56 is established, control data can be transferred to the microprocessor 50 and/or memory device 52; and data stored in the memory device 52 or otherwise available from the microprocessor 50 can be transferred to the external programmer. In this way, the device 12 is not only programmable, but its operating status and other data, such as EGM data, can be transmitted and recorded at an external location.

A pulse width and amplitude control circuit 58 is coupled to the microprocessor 50. The pulse control circuit 58 generates a pulse having an amplitude ("A")

and pulse width ("PW") defined by the microprocessor 50 whenever a trigger signal "T" is received from the microprocessor 50. Such pulse is directed to a pulse amplifier 60. The pulse amplifier 60 then delivers the desired pulse amplitude and width to the heart over the pacing lead 18.

A sense amplifier 62 is also coupled to the pacing lead 18. Thus, any electrical signals appearing on the pacing lead 18 that represent cardiac activity (i.e., an R-wave) may be sensed by the sense amplifier 62. The output of the sense amplifier 62 is a signal that is directed to the microprocessor 50. Thus, whenever an R-wave or other cardiac activity is sensed, the microprocessor 50 is alerted of such fact.

As further seen in FIG. 3, and as is commonly practiced in the pacemaker art, the microprocessor 50 further generates a blanking signal coincident with the generation of the trigger signal "T." Such blanking signal is directed to the sense amplifier 62. It is the function of the blanking signal, depicted as the signal "BLANK" in FIG. 3, to disable or blank the sense amplifier at the same time that the pulse amplifier 60 is delivering a stimulation pulse to the heart, and for a short time thereafter. Without a blanking signal, or equivalent, the sense amplifier 62 would sense the large amplitude pacing pulse when generated, and its sensing circuits would become saturated.

Still referring to FIG. 3, an oscillator circuit 64 is used to define the basic timing interval used by the microprocessor 50. Such oscillator circuit 64 is preferably realized using a crystal oscillator (XTAL OSC) to provide a stable timing base. The output of the oscillator 64 functions as a clock signal for operating the microprocessor, as well as for clocking any counters or timing circuits that are included as part of, or coupled to, the microprocessor 50.

The microprocessor 50 also generates an ICD trigger signal to enable a "defibrillation" charge circuit 66. The defibrillation charge circuit 66 controls the charging of an output capacitor 68, or equivalent charge storage device, from the battery (not shown in FIG. 3) of the ICD/pacing device 12. With the output capacitor 68 fully charged, the microprocessor 50 issues a "discharge" signal whenever a shocking pulse is needed. Such discharge signal effectively closes a discharge switch 70 that is connected between the output capacitor 68 and the defibrillation leads 26 and 28. The closing of the discharge switch 70 thus transfers the charge stored on the output capacitor 68 to the defibrillation electrodes 30 and 32. The defibrillation charge circuit 66 and discharge switch 70 are of conventional design.

It is to be emphasized that the microprocessor-based embodiment of the ICD/pacemaker device 12 shown in FIG. 3 is only representative of one possible embodiment of the device 12. Any design or configuration that provides the functions described above in connection with FIG. 2, or equivalents thereof, whether using a programmable microprocessor or not, may effectively be used to realize the ICD/pacemaker device of the present invention.

As discussed above, one of the problems of providing both bradycardia pacing support from a pacemaker concurrent with defibrillation support from an ICD, is determining when a shocking pulse is required. Normally, the ICD provides a shocking pulse when it to senses an arrhythmia, e.g., tachycardia or fibrillation. In the presence of a low amplitude ventricular fibrillation, the R-waves associated with the fibrillation, even though present, may be of insufficient amplitude to be sensed. Hence, the pacemaker responds by providing stimulation pulses at the pacing rate in an attempt to stimulate the heart.

Figure 4:
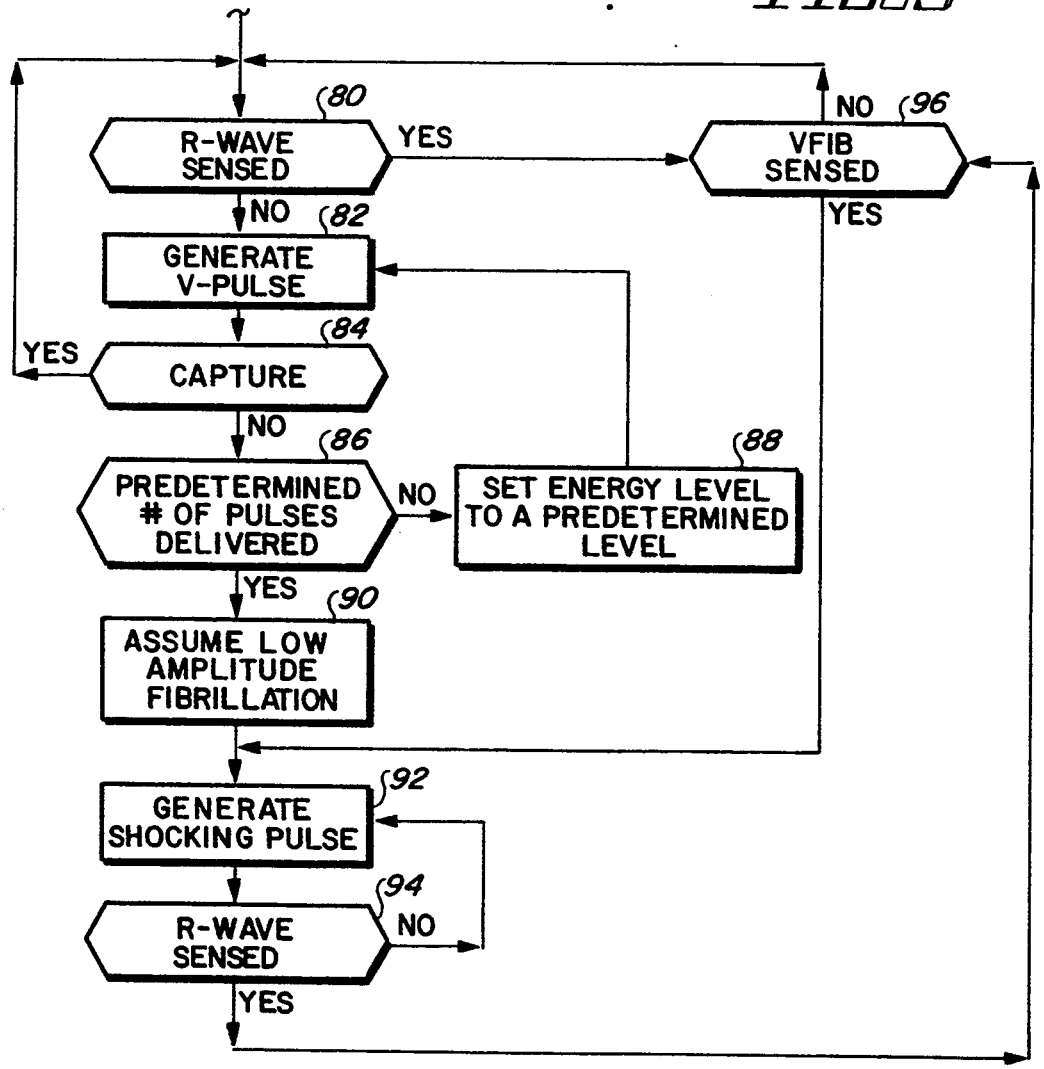
FIG. 4 is a simplified flowchart showing the technique used by the present invention for sensing and responding to low amplitude ventricular fibrillation.

Thus, according to another embodiment of the present invention, a method of detecting and responding to low amplitude ventricular fibrillation (i.e., ventricular fibrillation characterized by R-waves of insufficient amplitude to be sensed) is provided. Such method is depicted in the simplified flowchart of FIG. 4. In FIG. 4, each main step of the method is represented as a "block." For explanation purposes, each block has a reference number associated therewith. Further, in typical flowchart form, each block represents either a step that is performed (rectangular shaped block) or a decision that is made (diamond shaped block).

As seen in FIG. 4, the method includes a first step of determining if an R-wave has been sensed (block 80). If so, then a second determination (block 96) involves determining whether such detected R-wave is indicative of ventricular fibrillation ("V-Fib"). Such determination, which is based on the rate at which the R-waves occur, is typically made by examining the detection of several R-waves in succession using appropriate fibrillation-detection criteria (such as looking for at least a series of consecutive R-waves at a rate faster than a prescribed rate). Any suitable technique may be used for this purpose, as taught, for example, in U.S. Pat. Nos. 4,712,556 or 4,788,980. If the detected R-wave does not indicate the presence of ventricular fibrillation, then the method returns to the first step to see if another R-wave is sensed (block 80). If the detected R-wave does indicate the presence of ventricular fibrillation, then a shocking pulse is generated (block 92). After the shocking pulse is generated, a determination is made as to whether such shocking pulse was effective at stopping the ventricular fibrillation. Typically, this is done by determining if another R-wave is sensed (block 94). If no R-wave is sensed, another shocking pulse is generated (block 92). If an R-wave is sensed, then another determination is made as to whether such sensed R-wave indicates the presence of ventricular fibrillation (block 96), and the process repeats as described above.

As described thus far, the method depicted in FIG. 4 for detecting and responding to ventricular fibrillation presupposes that an R-wave has been sensed, that is, that an R-wave has sufficient amplitude and slew rate associated therewith to be detected. As such, those portions of the method shown in FIG. 4 that rely upon a detected R-wave, as described above, are not significantly different from the methods used by existing implantable pacemakers and ICD devices, as taught, for example, in U.S. Pat. No. 4,989,602.

The features of the present invention that are different from prior pacing and ICD devices and methods relate to how the pacing and defibrillation method responds if an R-wave is not sensed. As with all pacemakers operating in a demand mode of operation, if an R-wave is not sensed (block 80) before the termination of a designated escape interval, a ventricular stimulation pulse (V-pulse) is generated (block 82). Unlike known pacemakers, the present invention includes the step of determining if the V-pulse has effectuated capture (block 84). If capture has occurred, then the escape interval is restarted and the method returns to looking for the occurrence of an R-wave (block 80). If capture has not occurred (block 84), then a determination is made as to whether a predetermined number of pulses (block 86) have been delivered and the energy level is adjusted according to a predetermined sequence (block 88). In the simplest embodiment, at least one pulse is delivered at the highest energy level at which capture can be reliably detected. In an alternative embodiment, at least three pulses are delivered at the highest energy level at which capture can be reliably detected to prevent a single "non-capture" from falsely triggering a shocking pulse. In yet another embodiment, a programmable number or sequence of pulses may be delivered, each pulse having an increased energy level.

Once the predetermined number of pulses and energy levels have been delivered, and capture has still not occurred, then the method of the invention presumes that low amplitude ventricular fibrillation must be present (block 90). Absent a catastrophic malfunction in the pacing and sensing circuits (such as a broken pacing/sensing lead), such presumption has a high probability of being accurate. Further, many modern pacing devices include means for sensing a catastrophic malfunction, such as a broken or damaged pacing lead (see, for example, U.S. Pat. No. 4,899,750). Advantageously, such malfunction sensing means may be used in combination with the method of the present invention to further enhance the likelihood that the presumption made at block 88 of FIG. 4 is correct.

After the presumption has been made that a low amplitude ventricular fibrillation is present (block 90), a shocking pulse is generated (block 92). If the shocking pulse is effective at terminating the low amplitude ventricular fibrillation, then R-waves should again be detectable. If an R-wave is sensed (block 94), and if the frequency of occurrence of such sensed R-wave does not represent a high amplitude (i.e., detectable R-wave) ventricular fibrillation (block 96), then the method continues as described above, beginning at block 80, by looking for the occurrence of a subsequent R-wave. Should the shocking pulse not be effective at terminating the low amplitude ventricular fibrillation, then no detectable R-waves will occur, and an R-wave will not be sensed (block 94). If an R-wave is not sensed within a prescribed time period, then another shocking pulse is generated (block 92) in a further attempt to terminate the low amplitude ventricular fibrillation. So long as an R-wave is not sensed after generating a shocking pulse, additional shocking pulses will continue to be generated (blocks 92, 94) for so long as the system allows before disengaging.

Figure 5:
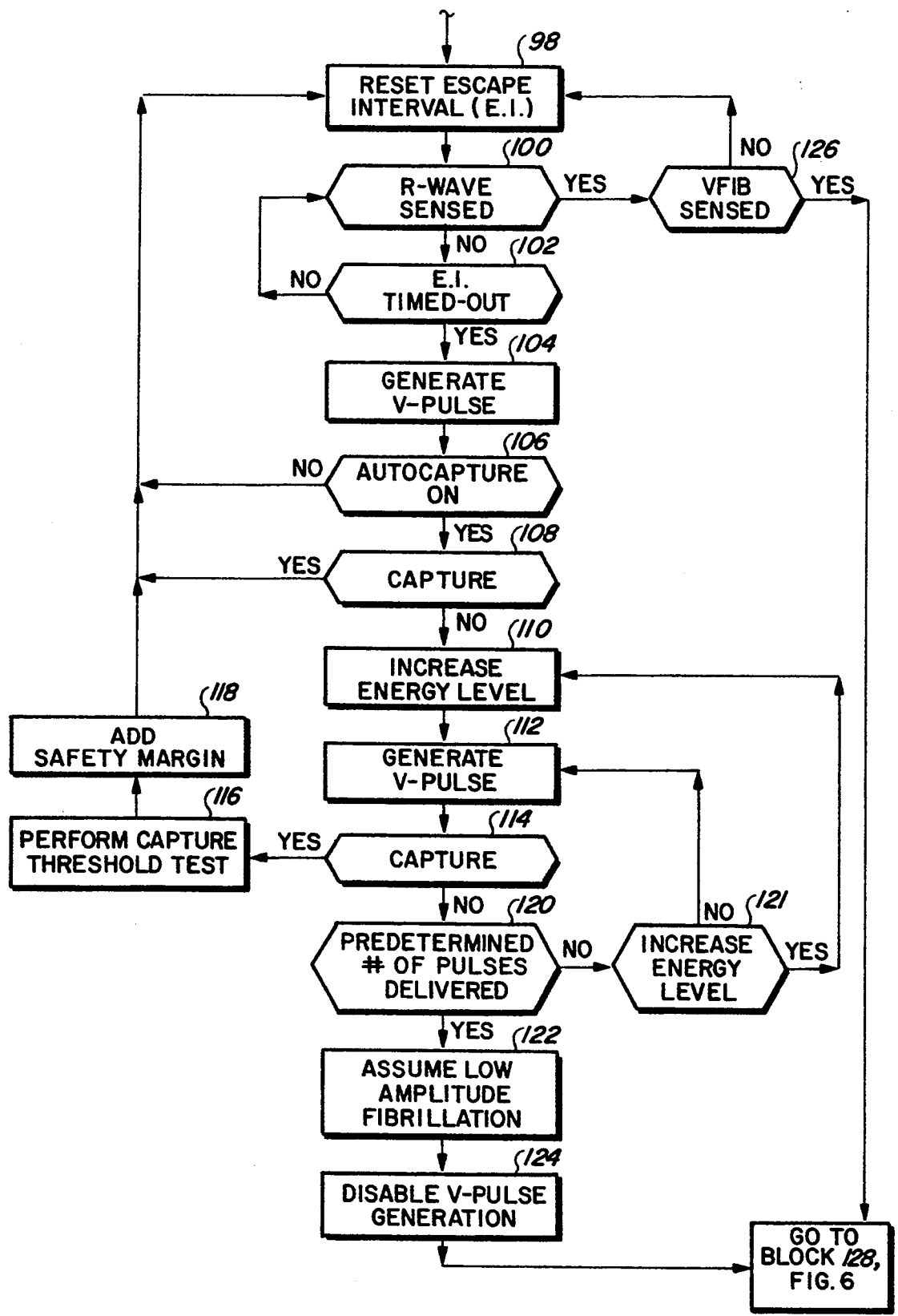
FIGS. 5 and 6 provide a more detailed flowchart showing the technique of FIG. 4.
Figure 6:
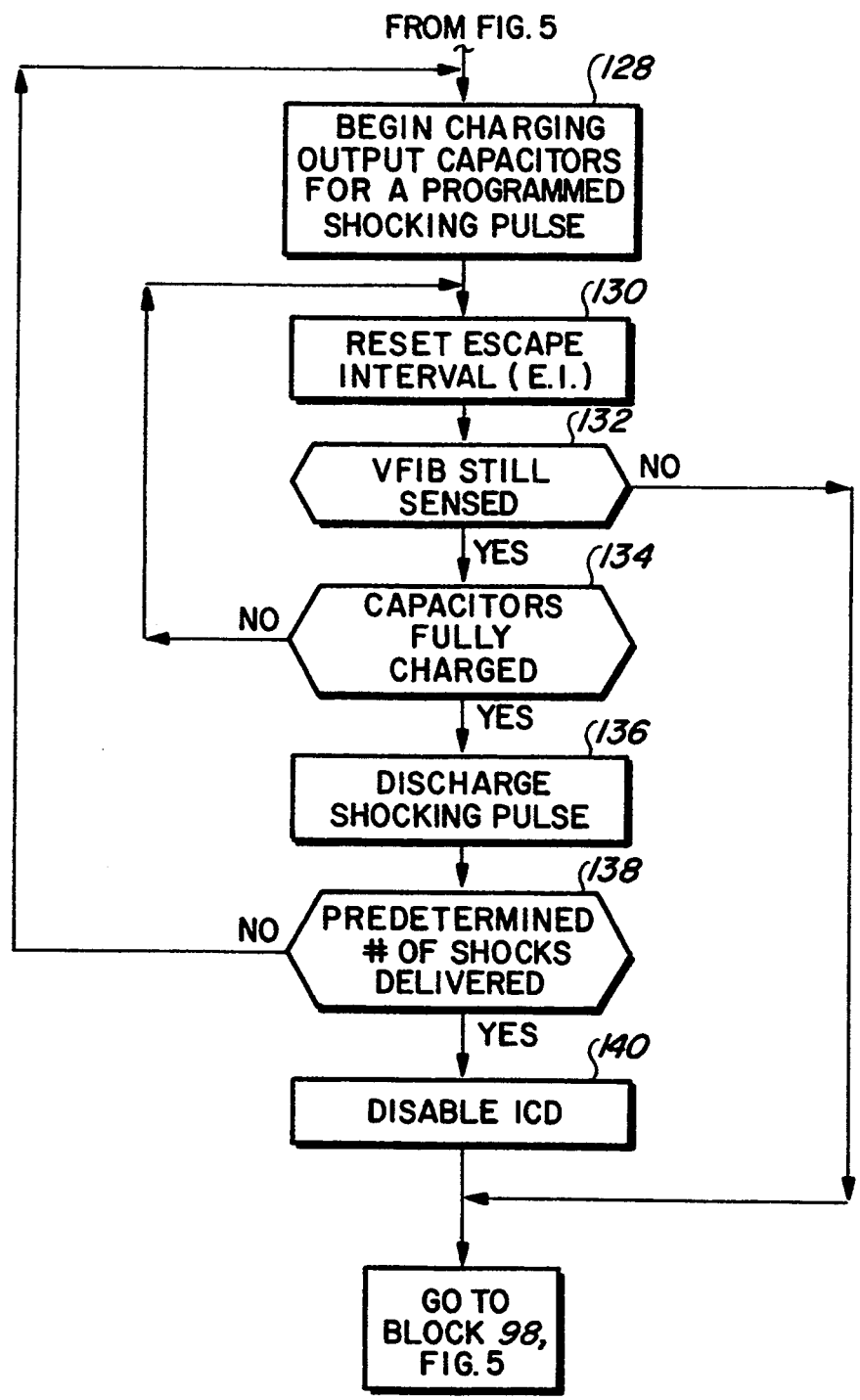

In FIGS. 5 and 6, a more detailed flowchart showing the technique and additional features of the present invention of FIG. 4 is presented. It is to be emphasized that because the present invention is adapted for use with implantable programmable pacer/ICD devices, the invention may be programmed ON or OFF. If programmed OFF, then the pacer and/or ICD device performs its pacing and sensing functions in a conventional way. If programmed ON, then the pacer/ICD device implements its capture-determining feature, and uses such feature to determine if low amplitude ventricular fibrillation is present.

As shown in FIG. 5, the method begins by resetting the escape interval, EI, (block 98) and by making a first determination as to whether an R-wave has been sensed during the programmed escape interval (blocks 100, 102). If an R-wave is sensed before the escape interval times-out, then a determination is made whether the frequency of occurrence of such detected R-wave represents ventricular fibrillation (block 126). This determination may be made in the same manner as described above in connection with FIG. 4. Assuming that ventricular fibrillation is not present, as determined at block 126, the escape interval is reset (block 98), and the process of looking for the occurrence of an R-wave during the escape interval begins again (blocks 100, 102).

If the escape interval times-out without sensing an R-wave, a V-pulse is generated (block 104). If the capture-determining feature (autocapture) has not been programmed ON (block 106), then the generation of the V-pulse also triggers the resetting of the escape interval (block 98), in conventional demand-mode pacer operation, and the process repeats. In this way, a V-pulse is continually generated on demand if an R-wave is not sensed during the prior escape interval. The above-described process of generating a V-pulse on demand is, of course, well understood and known in the art.

To better appreciate how the present invention modifies this process in order to detect and respond to a low amplitude ventricular fibrillation, concurrent reference will also be made to the timing waveform diagrams of FIGS. 7–11 as the remainder of FIGS. 5 and 6 are explained. It is noted that, in general, FIGS. 7–11 each show a simplified representation of: (1) the electrocardiogram (ECG) sensed at the skin of the patient using conventional electrocardiograph equipment; (2) the EGM, sensed by the pacemaker sensing circuits; (3) the escape interval (EI); and (4) output signals used with the present invention for a particular condition. The horizontal axis represents time, while the vertical axis represents the amplitude of the particular signal indicated (e.g., the ECG or EGM signal, or the stimulation pulse or shocking pulse generated (labeled "output")). The escape interval, EI, is represented in FIGS. 7–11 as a horizontal line terminated by a solid circle (if the escape interval is terminated by a sensed event) or an arrowhead (if the escape interval timed-out without sensing a cardiac signal). A small vertical bar along this line indicates the initiation of the next escape interval.

Figure 7:
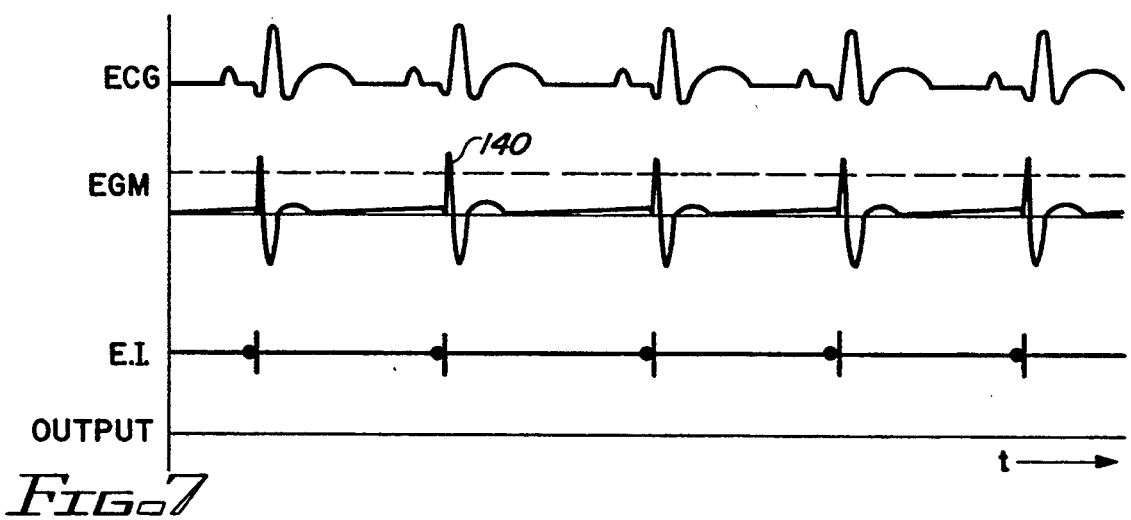
FIG. 7 is a timing diagram showing a simplified representation of the ECG, EGM, escape interval (EI) and output signals when R-waves occur prior to the timing-out of the escape interval.

Thus, with reference to FIG. 7, there is shown a heart condition where the heart generates R-waves 140 at an interval less than the pacemaker's escape interval (i.e., the heart rate is faster than the pacing rate, which inhibits an output). As shown in FIG. 7, the R-wave 140 is diagrammed as a biphasic waveform on the EGM, however, it should be noted that the exact waveform depends on the lead type and orientation. No output pulses are generated because an R-wave always occurs prior to the timing-out of the escape interval. Thus, with reference to the steps of the invention shown in the flowchart of FIG. 5, the condition shown in FIG. 7 corresponds to a repetition of the steps represented at blocks 98, 100 and 126.

Figure 8:
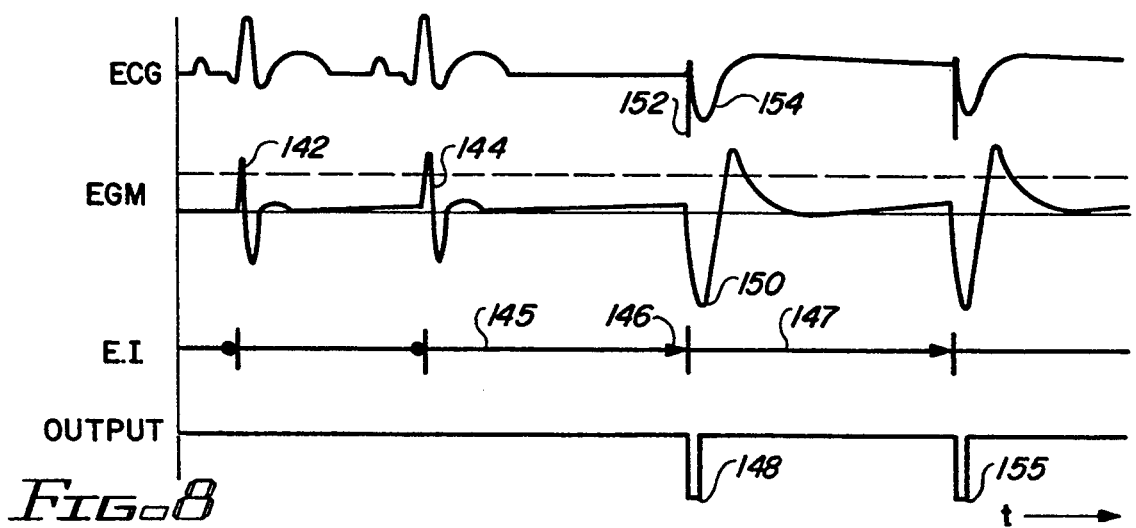
FIG. 8 is a timing diagram showing a simplified representation of the ECG, EGM, escape interval (EI) and output signals when R-waves occur at rates above and below the pacemaker's escape interval.

In FIG. 8, R-waves 142, 144 are generated at an interval less than the pacemaker's escape interval as shown in FIG. 7 for an initial cardiac cycle. (A "cardiac cycle" is the time interval that occurs between consecutive R-waves 142 and 144.) However, after R-wave 144, an escape interval 145 is begun that times-out before another R-wave is sensed, as indicated by the arrow 146. Hence, a stimulation pulse 148 is generated in order to evoke a ventricular contraction. Such ventricular contraction is diagrammed on the EGM waveform as an inverted R-wave 150. The stimulation pulse 148 is further evident in the ECG as a pulse 152, followed by an inverted R-wave 154. After the escape interval 145 times-out, a subsequent escape interval 147 is initiated that also times-out, causing another stimulation pulse 155 to be generated. For the condition shown in FIG. 8, this process repeats, with stimulation pulses being generated at the timing-out of each escape interval. The condition shown in FIG. 8 (beginning with the timing-out of the escape interval 145 and assuming that auto-capture is programmed ON (block 106)) corresponds to a repetition of the steps 98, 100, 102 104, 106 and 108 shown in FIG. 5.

Figure 9:
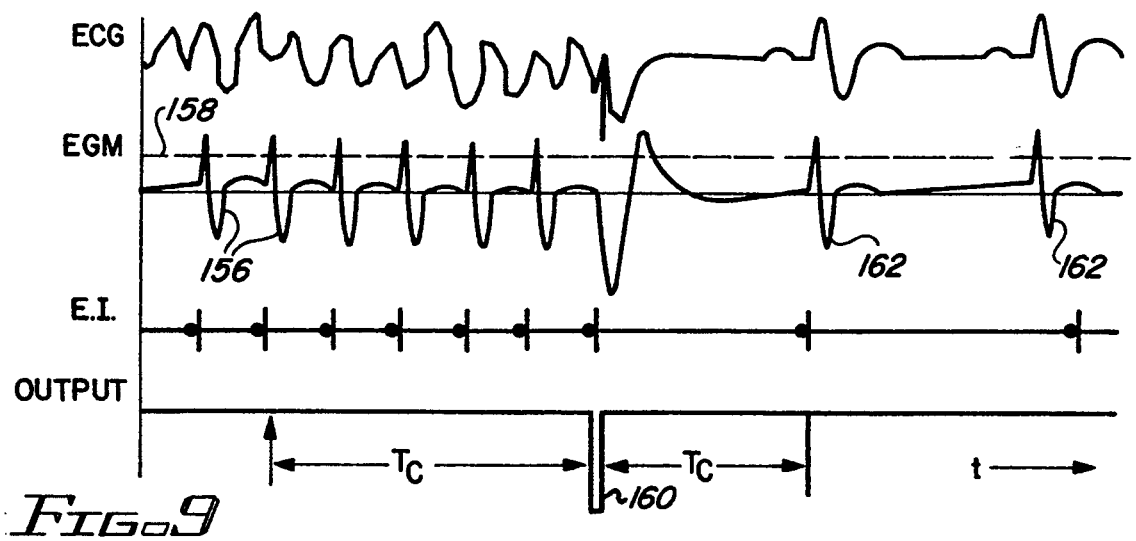
FIG. 9 is a timing diagram showing a simplified representation of the ECG, EGM, escape interval (EI) and output signals during sensed fibrillation signals.

In FIG. 9, a condition is shown that represents high level ventricular fibrillation. That is, as seen best in the EGM, a series of R-waves 156 occur at a rapid rate. Such R-waves 156 have a sufficiently high amplitude so as to be detectable. That is, the sensing circuits (36 of FIG. 2; or 62 of FIG. 3) have a threshold level associated therewith above which the amplitude of an R-wave must go if it is to be detected. Such threshold level is represented in FIG. 9 as the dashed line 158. Because the R-waves 156 have an amplitude that exceeds the threshold level 158, they are detected by the appropriate sensing amplifier. Hence, a ventricular fibrillation condition is sensed and a shocking pulse 160 is generated. As shown in FIG. 9, the sensed R-waves 156 continue at a rapid rate (i.e., a rate that is sufficiently high to comprise fibrillation) for a prescribed time period $T_C$ before the shocking pulse is generated. Typically, the time period $T_C$ corresponds to the time it takes to charge the output capacitor 68 of the defibrillation charge circuit 66 (FIG. 3). During the time period $T_C$, the system preferably looks for R-waves continuously, as described in FIGS. 5 and 6, However, it is also known in the art to simply verify ventricular fibrillation at the end of the charging cycle. For the condition shown in FIG. 9, the shocking pulse 160 is effective at stopping the ventricular fibrillation, as shown on the EGM waveform by the occurrence of normal R-waves 162 at a normal rate subsequent to the generation of the shocking pulse 160.

The condition represented in FIG. 9 (of sensing ventricular fibrillation, delivering a shocking pulse, and detecting normal cardiac rhythm) corresponds to the steps shown in blocks 98, 100, 126, 128, 130, 132, 134, 136, 138, 128, 130, 132 and 98 of FIGS. 5 and 6. That is, once a determination is made that ventricular fibrillation is present (block 126, FIG. 5), the output capacitor(s) of the defibrillation output circuit begins charging (block 128, FIG. 6). During the charging period, which typically requires a time $T_C$, the system preferably continuously checks for R-waves (blocks 130, 132) and will abort the shocking pulse if ventricular fibrillation is no longer detected. If the system still detects ventricular fibrillation (block 132) and such capacitor(s) become fully charged (block 134), then a shocking pulse is delivered (block 136). In anticipation of the next shocking pulse, the system preferably begins charging the output capacitor(s) for the next pulse (block 128). The escape interval is then reset and the system looks for a normal R-wave (blocks 132). If ventricular fibrillation continues, the system will deliver, preferably, only a predetermined number of shocks (block 138) before disabling the ICD circuitry (block 140).

As further shown in FIG. 5, if the capture-determining feature of the invention is programmed ON (block 106) (thus, enabling the present invention), then a capture test is performed (block 108) subsequent to the generation of the V-pulse (block 104). Such test determines whether the most recently generated V-pulse has caused capture. Several capture-determining tests may be used for this purpose, such as the one disclosed, for example, in U.S. Pat. No. 4,686,988; or in the copending U.S. patent application of Kleks et al., Ser. No. 07/980,941, filed Nov. 23, 1992, entitled "Autocapture System for Implantable Pacemaker." The '988 patent and the Kleks et al. "Autocapture System for Implantable Pacemaker" patent application are both assigned to the same assignee as is the present application, and both are incorporated herein by reference.

If the capture test indicates that capture has occurred (block 108), then the escape interval is reset (block 98), and the process continues as described above, looking for the occurrence of an R-wave during the new escape interval (blocks 100, 102). If capture has not occurred (block 108), then the energy level is increased (block 110), a new V-pulse is generated at the higher energy output, and the another capture test is performed (blocks 110, 112 and 114). Next, a determination is made as to whether a predetermined number of pulses (block 120) have been delivered. If not, then a determination (block 121) is made as to whether the energy level should be increased again (block 110) or whether to simply generate the V-pulse at the same level and repeat the test (block 112, 114).

As mentioned above, there are numerous combinations of pulse energies and number of pulses that may be contemplated to ensure against false-positives (i.e., falsely detecting a low amplitude fibrillation). Four examples include delivering: (1) at least one pulse at the highest energy level at which capture can be reliably detected; (2) at least three pulses at the highest energy level at which capture can be reliably detected to prevent a single "non-capture" from falsely triggering a shocking pulse; (3) a sequence of pulses, each pulse having an increased energy level; and (4) a programmable number pulses, each pulse having a programmable energy level.

If after a determination is made that capture has not occurred (at block 114) and all the combinations of pulse energies have been delivered (block 120), then the presence of a low amplitude ventricular fibrillation is presumed (block 122). In response to this presumption, the generation of further V-pulses is inhibited (block 124), and the output capacitor(s) begin charging (block 128, FIG. 6) in anticipation of delivering a shocking pulse (blocks 130, 132, 134, 136 and 138), and as described above in conjunction with FIGS. 6 and 9.

Figure 10:
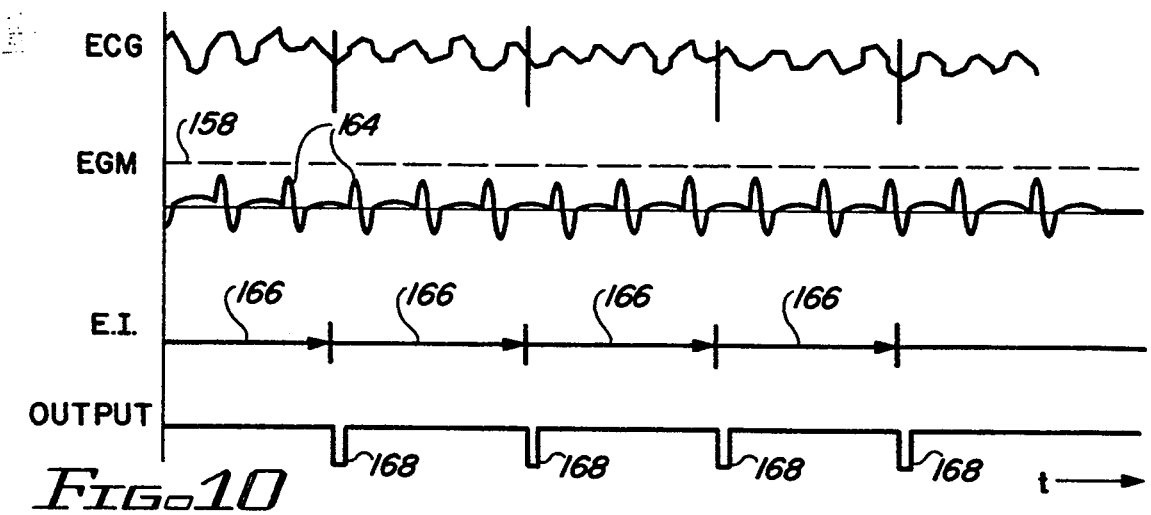
FIG. 10 is a timing diagram showing a simplified representation of the ECG, EGM, escape interval (EI) and output signals during low amplitude fibrillation signals that are not sensed.

In FIG. 10, a low amplitude ventricular fibrillation condition is shown. R-waves 164 occur at a rapid rate, as best evident from the EGM signal, but such R-waves have insufficient amplitude to be sensed by the sensing amplifier. That is, the amplitude of the low amplitude R-waves 164 is less than the threshold level 158 associated with the sensing amplifier. Hence, an escape interval 166 times-out (as indicated by the arrow), a stimulation pulse (V-pulse) 168 is generated, and the process repeats. Of course, the V-pulses 168 are ineffective at terminating the ventricular fibrillation. Without determining whether capture has occurred, the ventricular fibrillation will go undetected.

Figure 11:
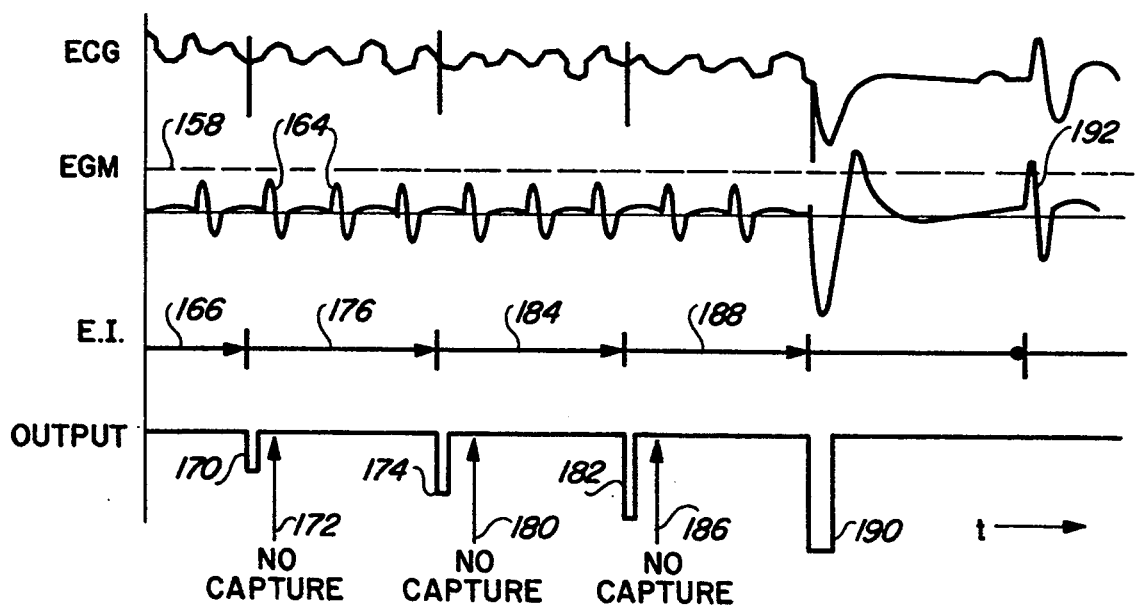
FIG. 11 is a timing diagram showing a simplified representation of the ECG, EGM, escape interval (EI) and output signals during low amplitude fibrillation signals that are not sensed using the present invention.

The present invention uses the method described above in connection with FIGS. 5 and 6 to generate a shocking pulse even when the low amplitude R-waves cannot be sensed. The effects of applying this method are illustrated in the timing waveform diagram of FIG. 11. As with the condition shown in FIG. 10, the condition shown in FIG. 11 is initiated by the occurrence of low amplitude R-waves 164 that have an amplitude less than the sensing threshold. Hence, the escape interval 166 times-out, and a stimulation pulse 170 is generated. In response to the stimulation pulse 170, the capture-determining technique makes a determination, for example, at time 172, that the stimulation pulse 170 did not effectuate capture. In response, the next stimulation pulse 174, generated at the conclusion of the next escape interval 176, has a higher energy content than the previous stimulation pulse 170. The stimulation pulse 174 fails to effectuate capture, as determined at time 180. Hence, a stimulation pulse 182, generated at the timing-out of escape interval 184, is of an even higher energy content. For the condition shown in FIG. 11 the stimulation pulse 182 represents the maximum possible stimulation pulse at which capture can be reliably detected. This maximum output pulse 182 also fails to effectuate capture, as determined at time 186. Hence, it is assumed that the heart is in low level fibrillation (block 122, FIG. 5). When the output capacitor(s) 68 becomes fully charged (block 134, FIG. 6), a shocking pulse 190 (block 136) is generated. As depicted in FIG. 11, the shocking pulse 190 is successful at terminating the low amplitude ventricular fibrillation, as characterized by the normal amplitude R-wave 192 that occurs thereafter. The sequence of pulses shown in FIG. 11 (i.e., the three pulses of increasing energy) are for illustration purposes only, since a plurality of combinations of pulse energy and number of pulses are possible.

As described above, it is thus seen that the present invention provides an implantable pacing and cardioversion device or method that automatically affords a patient appropriate therapy, either in the form of stimulation pulses on demand or shocking pulses as required. Advantageously, such device or method not only generates stimulation pulses on demand, but also ascertains the presence of, and responds to, ventricular fibrillation, regardless of whether such ventricular fibrillation is characterized by high or low level R-waves. That is, such device or method presumes the presence of low amplitude ventricular fibrillation even when the amplitude of the R-waves associated with such ventricular fibrillation are too low to be sensed using the normal sensing circuits of the device.

As further described above, it is seen that the present invention advantageously provides an implantable device that, while performing the functions of both a pacemaker and cardioversion/defibrillation device, minimizes the likelihood that the cardioversion/defibrillation device might sense and falsely interpret stimulation pulses generated by the pacemaker as cardiac activity.

Additionally, as described above, it is seen that the present invention provides an implantable pacemaker and cardioversion/defibrillation device that includes means for determining whether a given pacing pulse has caused capture.

While the invention herein disclosed has been described by means of specific embodiments and applications thereof, numerous modifications and variations could be made thereto by those skilled in the art without departing from the scope of the invention set forth in the claims.

What is claimed is:

1. A method for use within an implantable stimulation device for determining and responding to a first type of cardiac fibrillation, the implantable stimulation device having sensing means for sensing cardiac activity and pacing means for generating pacing pulses on demand, the first type of cardiac fibrillation being characterized by a low amplitude cardiac activity that cannot be sensed by the sensing means, the method comprising the steps of:
 (a) generating a pacing pulse if the sensing means fails to sense cardiac activity during a preset escape interval;
 (b) detecting if the pacing pulse generated in step (a) has caused capture; and
 (c) determining the presence of the first type of cardiac fibrillation in the event that capture has not occurred.

2. The method, as set forth in claim 1, further comprising the steps of:
 increasing, in response to step (b) detecting non-capture, the energy level of at least one pacing pulse to a predetermined value, and repeating steps (a) and (b) with the increased energy level pacing pulse; and
 determining the presence of the first type of cardiac fibrillation only if the increased energy level pacing pulse has not caused capture.

3. The method, as set forth in claim 2, wherein the increasing step comprises the step of:
 increasing the energy level of the at least one pacing pulse to an energy level at which capture can be detected and is expected to occur.

4. The method, as set forth in claim 1, further comprising the steps of:
 generating, in response to step (b) detecting non-capture, a series of pacing pulses, each pacing pulse having a successively higher energy level, and repeating steps (a) and (b) for each higher energy level pacing pulse; and
 determining the presence of the first type of cardiac fibrillation only if the series of higher energy level pacing pulses have not caused capture.

5. The method, as set forth in claim 4, wherein the pacing means includes means for programming the energy level for each of the series of pacing pulses, the method further comprising the step of:
 adjusting the energy level for each of the series of pacing pulses according to the programmed energy levels.

6. The method, as set forth in claim 4, wherein the pacing means includes means for programming a predetermined number of pacing pulses to form the series of pacing pulses, the method further comprising the step of:
 generating the series of pacing pulses according to the programmed predetermined number.

7. The method, as set forth in claim 6, wherein the step of adjusting the series of pacing pulses comprises the step of:
 adjusting the series to include at least three pacing pulses.

8. The method, as set forth in claim 1, further comprising the steps of:
 generating, in response to step (b) detecting non-capture, at least three pacing pulses, each pacing pulse having a predetermined energy level, and repeating steps (a) and (b) for each pacing pulse; and
 determining the presence of the first type of cardiac fibrillation only if the at least three pacing pulses have not caused capture.

9. The method, as set forth in claim 1, further comprising the steps of:
 generating, in response to step (b) detecting non-capture, at least three pacing pulses of equal value, and repeating steps (a) and (b) for each pacing pulse; and determining the presence of the first type of cardiac fibrillation only if the at least three pacing pulses of equal value have not caused capture.

10. The method, as set forth in claim 9, further comprising the step of:

increasing the energy level of the at least three pacing pulses to an energy level at which capture can be detected and is expected to occur.

11. The method, as set forth in claim 1, further comprising the steps of:

(d) sensing cardiac activity indicative of a second type of cardiac fibrillation, the second type of cardiac fibrillation being characterized by a sustained rhythm of high amplitude cardiac activity that can be sensed by the sensing means at a rate faster than a prescribed rate;

(e) ceasing the generation of pacing pulses upon determining the first type of cardiac fibrillation or upon sensing the second type of cardiac fibrillation; and (f) generating a shocking pulse in order to terminate one of the first or the second type of cardiac fibrillation.

12. A method for use within an implantable stimulation device for detecting and responding to ventricular fibrillation when R-waves associated with such ventricular fibrillation are sufficiently low in amplitude to prevent their being sensed, the implantable stimulation device having sensing means for sensing cardiac activity, pacing means for generating pacing pulses on demand, and shocking means for generating a shocking pulse in order to terminate the ventricular fibrillation, the method comprising the steps of:

(a) determining if a given pacing pulse generated by the pacing means has caused capture;

(b) increasing the energy of the pacing pulses generated by the pacing means in the event capture does not occur in step (a);

(c) repeating steps (a) and (b) until either the energy of the pacing pulses has increased to a predetermine value or capture occurs; and (d) in the event capture does not occur, delivering a shocking pulse from the shocking means.

13. The method, as set forth in claim 12, further comprising the step of:

stopping the generation of the pacing pulses after the energy of the pacing pulses has increased to the predetermine value.

14. An implantable pacing and shocking device comprising:

sensing means for sensing cardiac activity, the sensing means including means for sensing a first type of cardiac fibrillation characterized by a sustained rhythm of cardiac activity at a rate faster than a prescribed rate;

pacing means for generating pacing pulses at a plurality of energy levels on demand;

means for generating shocking pulses upon sensing cardiac activity indicative of the first type of cardiac fibrillation; and determining means for determining the presence of a second type of cardiac fibrillation, the second type of cardiac fibrillation being characterized by a low amplitude cardiac activity that cannot be sensed by the sensing means, the determining means including:

capture-determining means for determining if a given pacing pulse generated by the pacing means has effectuated capture, the absence of capture corresponding to the second type of cardiac fibrillation and the presence of capture corresponding to an energy level that was too low to ensure capture, and decision-determining means responsive to the capture-determining means for determining the presence of the second type of cardiac fibrillation.

15. The implantable pacing and shocking device, as set forth in claim 14, wherein the presence of the second type of cardiac fibrillation is determined by the decision-determining means whenever a prescribed type of pacing pulse fails to effectuate capture.

16. The implantable pacing and shocking device, as set forth in claim 15, wherein the presence of the second type of cardiac fibrillation is determined by the decision-determining means whenever a prescribed number of pacing pulses fails to effectuate capture.

17. The implantable pacing and shocking device, as set forth in claim 15, wherein the decision-determining means determines the presence of the second type of cardiac fibrillation only when a pacing pulse of a predetermined high energy level fails to effectuate capture.

18. The implantable pacing and shocking device, as set forth in claim 15, wherein the pacing means includes means responsive to the capture-determining means for increasing the energy of a next pacing pulse whenever a preceding pacing pulse fails to effectuate capture.

19. The implantable pacing and shocking device, as set forth in claim 18, wherein the shocking means further includes means for generating a shocking pulse whenever the capture-determining means determines that the second type of cardiac fibrillation is present.

20. An implantable pacemaker and shocking device comprising:

pulse generator means for generating stimulation pulses on demand at a selected programmed energy;

autocapture means for determining whether a given stimulation pulse has effectuated capture;

first processing means responsive to a determination by the autocapture means that capture has not been effectuated by the given stimulation pulse, for automatically increasing the energy of a next stimulation pulse; and second processing means, responsive to a determination by the autocapture means that capture has not been effectuated by a stimulation pulse having a predetermined energy, for determining that a low amplitude ventricular fibrillation condition is present; and a high energy pulse generator means for generating a high energy shocking pulse in response to a determination by the second processing means that a low amplitude ventricular fibrillation condition is present.

* * * * *